United States Patent [19]

Scholze

[11] Patent Number: 4,833,323
[45] Date of Patent: May 23, 1989

[54] DETERMINING THE COMPOSITION OF A SOLID BODY

[75] Inventor: Christian Scholze, Munich, Fed. Rep. of Germany

[73] Assignee: Atomika Technische Physik GmbH, Oberschleissheim, Fed. Rep. of Germany

[21] Appl. No.: 113,674

[22] Filed: Oct. 26, 1987

[30] Foreign Application Priority Data

Oct. 27, 1986 [DE] Fed. Rep. of Germany ....... 3636506

[51] Int. Cl.$^4$ .............................................. H01J 37/26
[52] U.S. Cl. .................................. 250/309; 250/310; 250/307
[58] Field of Search ................. 250/306, 307, 309, 310

[56] References Cited

U.S. PATENT DOCUMENTS 3,881,108  4/1975  Kondo et al. ........................ 250/307
3,916,190  10/1975  Valentine et al. .................... 250/309
4,107,527  8/1978  Cherepin et al. .................... 250/292
4,661,702  4/1987  Welkie ................................ 250/309
4,683,378  7/1987  Shimase et al. ................. 250/492.21

OTHER PUBLICATIONS

"Scanning Electron Beam Lithography for Fabrication of Magnetic Bubble Circuits", Chang et al., *I.B.M. J. Res. Developement*, pp. 376-388, Jul. 1976.
"Automatic Electron Beam Fabrication of Micron-Size Devices," Wilson et al., *Conference Scanning Electron Microscopy*, 1976, pp. 659-668.

*Primary Examiner*—Bruce C. Anderson
*Attorney, Agent, or Firm*—Henry C. Nields

[57] ABSTRACT

A method of determining the composition of a solid body comprises guiding a primary ionic beam to impact on the body in a spiral path whereby secondary particles are released from the body which are detected and registered in dependence on the location of their release.

12 Claims, 4 Drawing Sheets

4,833,323

DETERMINING THE COMPOSITION OF A SOLID BODY

BACKGROUND OF THE INVENTION

I. Field of the Invention

The present invention relates to a method of determining the composition of a solid body or specimen, hereinafter also referred to as "target", which is scanned by a primary particle beam which causes secondary particles to be released which are detected and registered in dependence on the location of their release. More specifically the invention relates to methods of secondary ion mass spectroscopy (SIMS). The devices used for secondary ion mass spectroscopy are well known in the art and described, for example, in the periodical "The Review of Scientific Instruments", New York, vol. 42, no. 1, at pages 44 et seq.

II. Description of the Related Art

For the purpose of examining atomic or molecular concentrations in solid bodies, such as semiconductor materials, integrated circuits and the like, a primary particle beam is scanned over a field of a given size of the target. When the primary particles impact against the target, secondary particles, e.g. atoms or molecules, are released from it. A certain proportion of the secondary particles is ionised when they are knocked out of the target. The ions can be detected and analysed in a selective detector which is responsive to charged particles, e.g. in a mass selective detector comprising a Quadrupole mass filter and a photomultiplier dectector with an electronic counter. If the ionic concentrations are recorded in accordance with the location of their release the lateral distribution of the atomic or molecular concentrations in the target may be determined.

In an ionic beam scanning method disclosed in the Paper entitled "Time-of-Flight Effects in Quadrupole-Based Scanning Ion Microprobes", K. Wittmaack, SCANNING Vol. 3,2 (1980), an ionic beam is guided linearly over the field of the target to be scanned in a manner similar to the electron beam in a television tube. The secondary atoms or molecules are released, partially as secondary ions, at each point at which the primary ionic beam impacts on the test piece. Between the impact of the primary ionic beam on a surface element, hereinafter referred to as a "pixel", of the sample and the detection of the secondary particles in the detector a certain time elapses which is termed the "offset-time" $\Delta\tau$. The offset-time is dependent on the mass, energy and charge of the secondary ions and is naturally subject to a statistical distribution so that the offset-time $\Delta\tau$ is associated with a mean time error $\Delta t$. This means that the reliability with which secondary ions detected in the detector can be associated with a certain pixel decreases with an increase in the scanning velocity. In order to achieve a high locational resolution the primary ionic beam is therefore guided over the test piece with a relatively low scanning velocity.

The known secondary ionic mass spectroscopy method, known in short as the ionic beam scanning method, is an extremely versatile method. It is possible to register atomic or molecular concentrations in dependence on the location of the impact of the primary ionic beam and thus to examine their spatial distribution—both laterally with respect to the direction of the primary ionic beam and also over a certain depth of the test piece by removing the upper atomic or molecular layers. With the primary ion beam it is also possible to obtain a mass spectrum of the atomic or molecular concentration by registering the secondary ions in dependence on the mass of the secondary ions by tuning the Quadrupole mass filter.

By far the most frequent use nowadays of the ionic beam scanning method resides in increasing the material removal rate to such an extent by the use of a high primary ionic beam density that in the scanned field a "crater" forms from which a further layer of material is removed on each successive scanning. This enables one to obtain a depth profile of atomic or molecular concentration in the test piece.

In very many solids to be examined, e.g. semiconductor materials, which are doped by diffusion or ion implantation the concentration of the element to be examined varies within a thin surface layer by several orders of magnitude. It is therefore important when registering the secondary ions not to distort the result by submerging the measurements of the secondary ions of low concentration removed at a certain depth in the secondary ions of higher concentration removed from a lesser depth at the edge of the crater and thus to render the measured values unreliable.

In order that such "crater edge effects" can be eliminated a "window" or gate is set within the crater, generally in the center of the crater, which covers the surface of the entire field scanned by the primary ionic beam, the edge of which window is spaced far enough from the crater edge to eliminate as substantially as possible the impact of the crater edge effects. Thus only those secondary ions are registered which have been detected during the period of time which corresponds to that during which the primary ionic beam was within the window.

When scanning linearly, the primary ionic beam crosses the edge of the window twice in each line which covers the window, namely once at time $t_1$ on entering the window and a second time at time $t_3$ when leaving the window. The offset-time $\Delta\tau$, which depends on the mass, energy and charge of the secondary ions and in practice can only be measured with considerable difficulty, should thus be taken into account because at time $t_1$ on entry into the window those secondary ions are firstly detected which have been released from the test piece at a position which corresponds to the time $t_1 - \Delta\tau$. The same applies also to the time $t_3$ of the exit from the window. Since the offset time $\Delta\tau$ is associated with the time error $\Delta t$, the times $t_1$ and $t_3$ can only be determined with an accuracy $\Delta t$. The edges at the beginning and at the end of the window with respect to the direction of movement of the primary ionic beam are thus increasingly "blurred" with an increase of the time error $\Delta t$ with respect to the period of dwell of the primary ionic beam on a pixel. In order to maintain the position and shape of the window in the middle of the crater a relatively low scanning velocity is thus necessary when scanning linearly.

It is thus an object of the invention to provide a method of determining the composition of a solid body of the type described above in which the position and shape of the window do not vary with a substantially increased scanning velocity.

SUMMARY OF THE INVENTION

According to the present invention there is provided a method of determining the composition of a solid body in which a primary particle beam is guided to impinge against the body in a spiral path whereby secondary particles are released from the body which are detected and registered in dependence on the location of their release. The primary particle beam may be guided over the surface of the body to move inwardly along the spiral path and then subsequently outwardly the same or a different spiral path or in a substantially straight line directly back to the starting point.

BRIEF DESCRIPTION OF THE INVENTION

One embodiment of the invention will now be described below by way of example with reference to the accompanying drawings, in which.

DESCRIPTION OF PREFERRED EMBODIMENT

Figure 1:
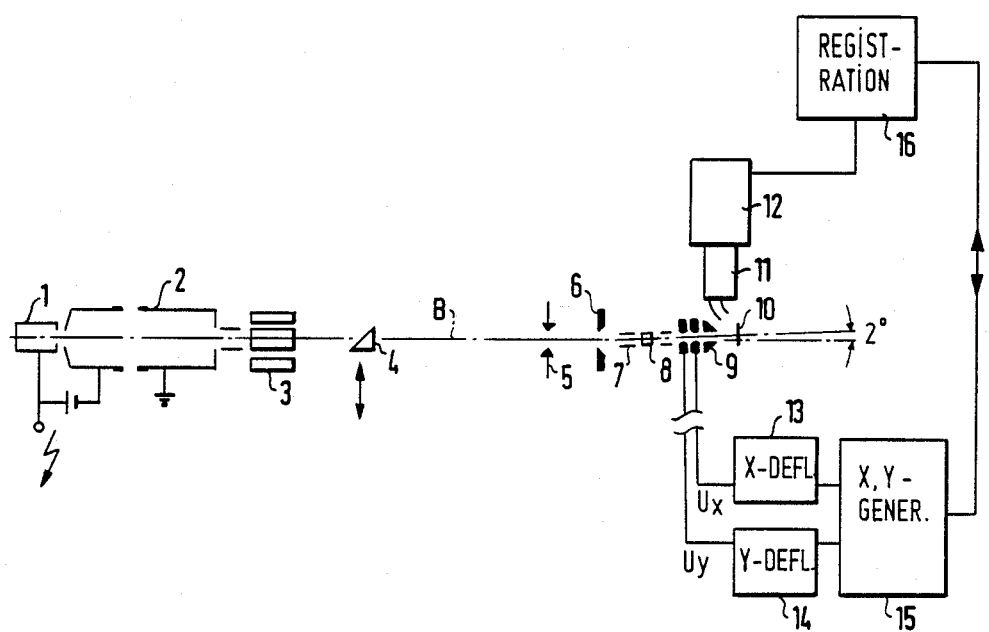
FIG. 1 is a schematic representation of a secondary mass spectrometer of the type suitable for carrying out the method in accordance with the invention.

The construction of a known secondary ionic mass spectrometer is shown schematically in FIG. 1. The spectrometer is received in a (not shown) ultra high vacuum system pumped by devices known in the art as a turbomolecular pump and a getter pump. The primary ionic beam B which may comprise oxygen, argon or cesium ions is produced in a plasma ionic source 1 and firstly passes through a beam shaping device comprising an immersion lens 2 and a Wien speed filter with a beam adjustment 3. After formation in the beam shaping device the beam then passes through a triangular prism 4 and a variable object aperture 5. The triangular prism 4 can, if required, be pivoted into the beam path to adjust the latter under visual control. The variable object aperture 5 serves to adjust the diameter of the primary ionic beam. After passing through a pressure step 6 which separates the primary ion beam producing system comprising the elements 1 through 5 which are under a vacuum of about $10^{-5}$ Pascal from the test piece and the analysing system under a vacuum of about $10^{-7}$ Pascal, the primary ionic beam is slightly deflected (in this case by 2°) from its original direction into a device 7 for suppressing neutral particles, whereby neutral particles are masked out from the further path of the primary ionic beam. After passing through an ionic lens 8 for fine focussing the primary ionic beam it passes into a deflecting device 9. In the deflecting device 9 the primary ionic beam is deflected from its original direction by two electric fields acting perpendicularly to one another similar to the electron beam in an oscilloscope and guided in a predetermined scanning pattern over the target or test piece 10. A proportion of the secondary ions knocked out of the test piece 10 on impact of the primary ionic beam thereon enter into a Quadrupole mass filter 11 after passing through a secondary ionic optical system (not shown). The Quadrupole mass filter 11 of a type known in the art as described, for example in U.S. Pat. No. 3,859,226 is adjustably selectively permeable only for secondary ions with a predetermined charge/mass ratio. The secondary ions permitted to pass by the Quadrupole mass filter 11 are detected in an ionic detector 12, e.g. a channel secondary electron multiplier (channeltron), as it is known e.g. from U.S. Pat. No. 4,652,788, and registered in a registration unit 16. The electric fields in the deflecting device 9 are produced by voltages $U_x$ and $U_y$ which are generated by a X-deflection driver stage 13 and a Y-deflection driver stage 14, respectively, in response to the output signals of a X, Y generator 15 of which one embodiment will be described later in detail.

Figure 2A:
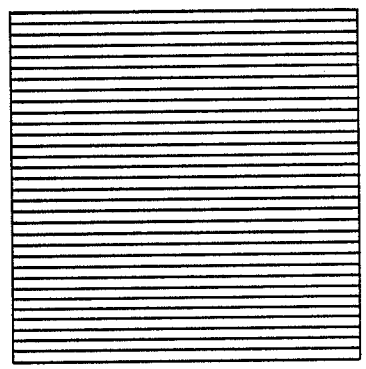
FIG. 2a is a schematic plan view of a field of a test piece scanned linearly by a primary ionic beam as known in the art.

Before the method of the present invention is described it will be helpful to consider the known method with linear scanning:

FIG. 2a shows schematically a field scanned by a primary ionic beam in which the beam is guided linearly over the field in a manner similar to the electron beam in a cathode ray tube. As an example, let it be supposed that the field is scanned with a resolution of 256 lines and each line contains 256 scanning spots or "pixels". For suppressing e.g. crater edge effects in the plotting of a profile of atomic or molecular concentrations in the test piece a "50% window" is set, i.e. a window, the length of whose sides is 50% of that of the scanned field, with correspondingly 128 pixels in each of the 128 lines. If one assumes that e.g. one second is used for scanning the entire field, then this means that the primary ionic beam is in each line for 1/256 s and thus for a duration of 1/512 s, i.e. around 2 ms, within the window in each line and during scanning enters and leaves the window 128 times each. The temporal gap between the impingement of the primary ionic beam on the crater edge and the entry of the primary ionic beam into the window is 1/1024 seconds, i.e. around 1 milllisecond. As mentioned above in connection with the crater edge effects, it is important that secondary ions released on impact of the primary ionic beam within the window at a particular depth of the test piece are registered separately from the ions which have been released on impingement of the primary ionic beam on the crater edge from a lesser depth.

In accordance to the principles of the present invention a beam of primary particles is guided over the surface of the test piece along a spiral path. A field in which a primary ionic beam is guided along a spiral path, in this case specifically on a quadrate path, is illustrated schematically in FIG. 3a. Beginning in one corner (the upper left corner in FIG. 3a) the primary ionic beam is guided in an uninterrupted track to the center of the field and from there outwardly again, the duration of dwell per surface element of the test piece, i.e. per pixel being the same for all pixels.

Figure 3A:
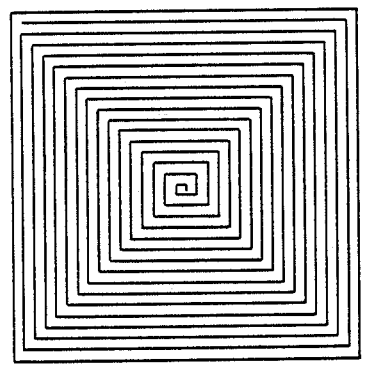
FIG. 3a is a schematic plan view of a spirally scanned field in accordance with the present invention.
Figure 4A:
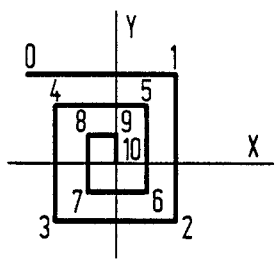
FIG. 4a is a schematic plan view which shows a part of a test field scanned spirally in accordance with the present invention.
Figure 4B:
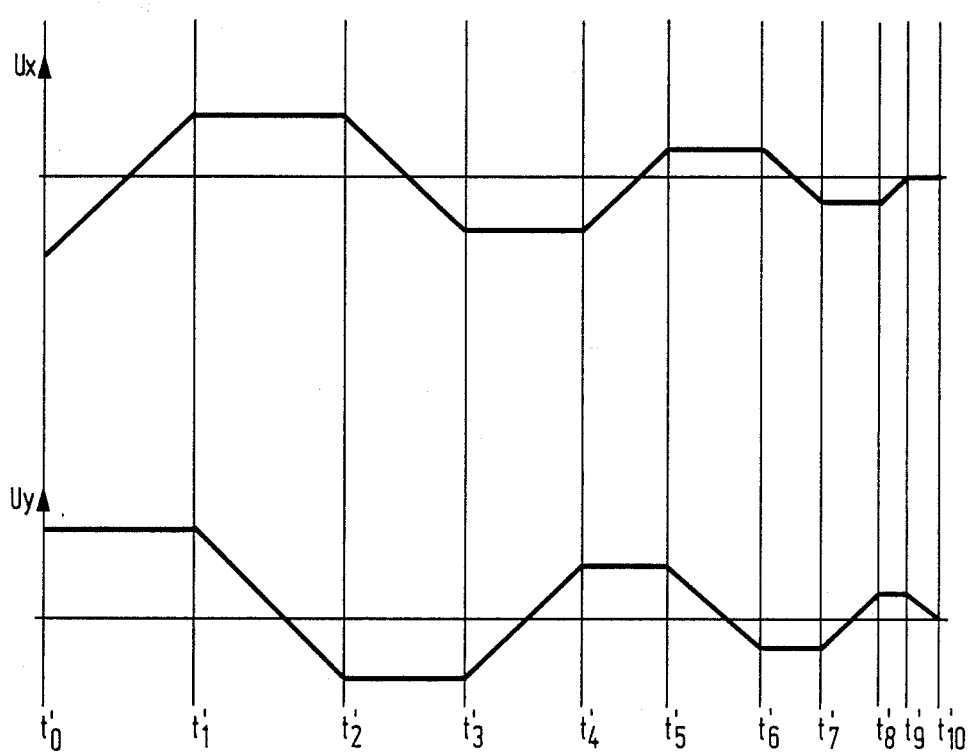
FIG. 4b is a diagram which shows the voltages versus time used for deflecting the primary particle beam of the apparatus in FIG. 1 along the spiral path of FIG. 4a in accordance with the present invention.

FIGS. 4a and 4b show the (still more schematized) spiral path of the primary particles as in FIG. 3a and the voltages used for deflecting the primary beam in the deflecting device 9 of FIG. 1, respectively. Beginning in the upper left corner at a point 0 at a time t⁰40 a voltage $U_x$ for deflection along the X axis linearly increases from a negative level corresponding to the X coordinate of point 0 until it reaches at a time $t_1'$ a level corresponding to the X coordinate at point 1, while during the time interval beginning at $t_o'$ and ending at $t_1'$ a voltage $U_y$ for deflection along Y axis remains constant at a positive level corresponding to the Y coordinate of the line 0-1. After reaching point 1 the voltage $U_x$ remains constant at a level corresponding to the X coordinate of point 1 during a time interval from $t_1'$ until $t_2'$, while the voltage $U_y$ at time $t_1'$ begins to decrease linearly from the level corresponding to the Y coordinate of point 1 until it reaches at a time $t_2'$ a level corresponding to the Y coordinate of point 2. This procedure correspondingly continues until at time $t_{10}'$ primary ion beam reaches the center of the field. Then the primary particle beam either may be guided from the center outwardly along the same or a different spiral path or in a substantially straight line directly back to the starting point.

Figure 5:
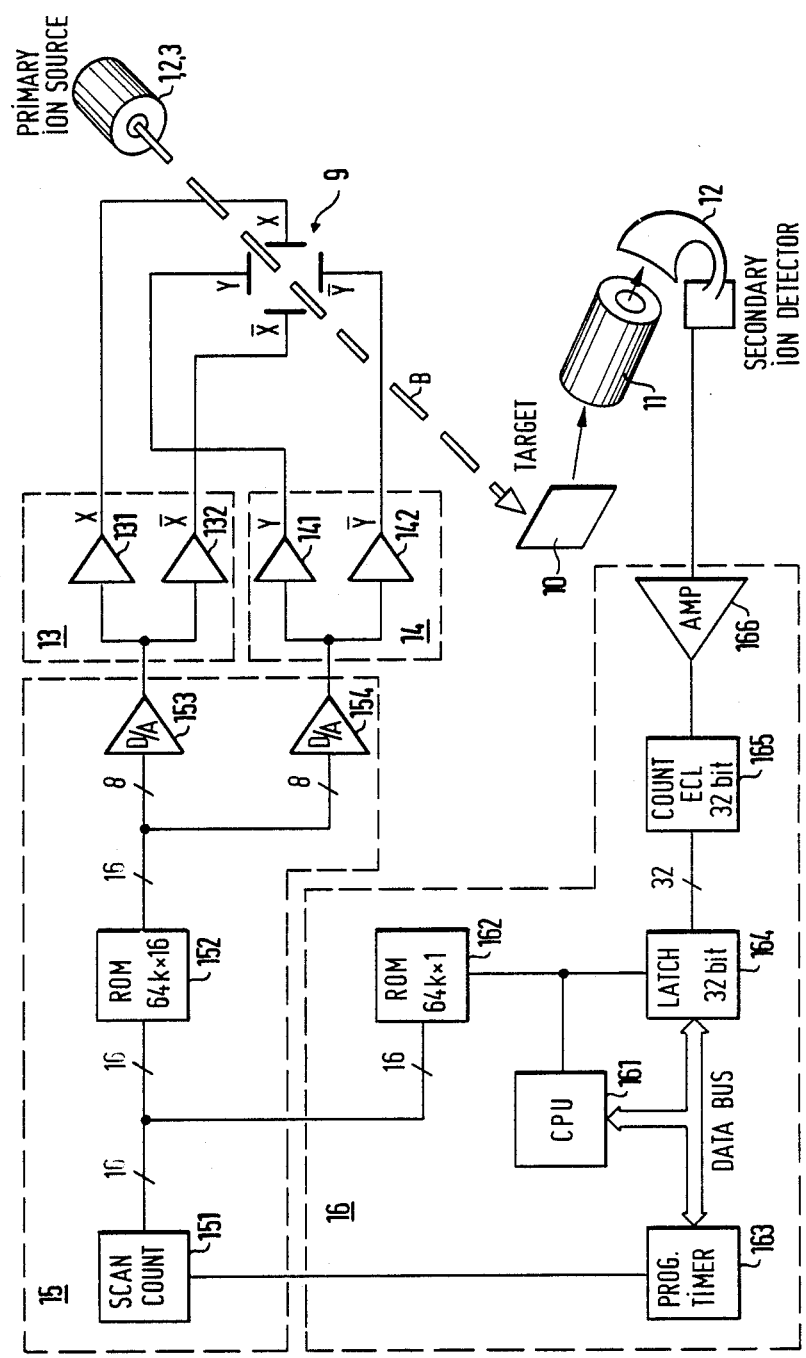
FIG. 5 is a block and partially schematic diagram showing one embodiment of an electronic circuit in a secondary ion mass spectroscopy apparatus which controls the primary ion beam and the registration of detected secondary ions in accordance with the present invention.

Referring to FIG. 5 now will be described one embodiment of a electronic circuit in a secondary ion mass spectroscopy apparatus which controls the deflection of the primary ion beam and which performs the registration of deflected secondary ions in accordance with the present invention. Elements like or similiar to these shown in FIG. 1 are designated by the like reference numerals. The primary ionic beam B leaving the ionic beam producing system which includes the ionic source 1 and the beam shaping device 2,3 is deflected from its original direction on the axis of the system by electric fields produced in the deflecting device 9. The electric fields acting perpendicular to one another are produced by two pairs of orthogonally arranged deflecting electrodes (similar as used in an electron beam oscilloscope) which are coupled to the outputs of the X and Y deflection driver stages 13 and 14, respectively. The X deflection driver stage 13 includes a non-inverting high voltage amplifier 131 and an inverting amplifier 132. The Y deflection driver stage 14 similarily includes a non-inverting high voltage amplifier 141 and an inverting amplifier 142. The outputs X and $\overline{X}$ of the amplifiers 131 and 132 are connected to one of the pair of the X deflection electrodes, respectively. The outputs Y and $\overline{Y}$ of the amplifiers 141 and 142, respectively, are connected to one of the pair of the Y deflection electrodes, respectively. The output voltages of the amplifiers 131, 132 and 141, 142 may be in the range of −200 volts to +200 volts. The X, Y generator 15 includes a scan counter 151, a read only memory (ROM) 152 and two digital-to-analog converters (D/A) 153 and 154. In the shown embodiment in which the field scanned on the target has 256 by 256 pixels which are 65 536 pixels, the scanned counter 151 is able to generate linear addresses from 0 to 65 535. The linear addresses are outputted from the scan counter 151 in a 16 bit parallel format. The ROM 152 which has a capacity of 64 k of 16 bits performs a mapping transformation from the linear addresses of scan counter 151 to addresses of the desired spiral path in an X, Y format of the raster coordinates of the 256 by 256 pixels. These spiral addresses are outputted from the ROM 152 in a 16 bit parallel format, too. The eight most significant bits are representing the X coordinate, the eight least significant bits are representing the Y coordinate of each pixel of the spiral path. The value of the X coordinate address is converted into an analog signal by the digital-to-analog converter 153, the Y coordinate address is converted into an analog signal by the digital-to-analog converter 154, the outputs of which are lying in a range between −10 volts and +10 volts. The output of the D/A 153 is coupled to both the amplifiers 131 and 132, the output of D/A 154 is coupled to both the amplifiers 141 and 142. When the scan counter 151 is started after receiving a starting signal from the registration unit 16 it begins to count all addresses from 0 to 65 535. Each of these linear addresses is transformed by ROM 152 into one of the 65 536 X, Y coordinate addresses of the spiral path to be scanned by the primary ion beam. Then these X, Y coordinate addresses are converted into analog signals and amplified for performing the deflection Then these X, Y coordinate addresses are converted into analog signals and amplified for performing the deflection of the primary ion beam. The registration unit 16 includes a central processing unit (CPU) 161 which controls the registration unit 16 and all the other functions of the secondary ion mass spectroscopy apparatus. Further the registration unit 16 includes a programmable timer 163, a read only memory (ROM) 162 with a capacity of 64 k of one bit, a 32 bit parallel latch 164, a 32 bit counter 165 and a pre-amplifier 166. A secondary ion released from the sample target 10 and passing the Quadrupole mass filter 11 and being detected in the secondary particle detector 12 results in one electric pulse or an "event", which is outputted from the detector 12. The events are extremely weak pulses, which after being amplified by the preamplifier 166 are counted into the particle counter 165. The output of the scan counter 151 also is coupled to the ROM 162 for generating gate pulses which provide an interrupt signal for the CPU 161 and in the same moment an activating signal for the latch 164. In response to each gate signal from ROM 162 the latch 164 makes a "copy on the fly" of the momentary content of the particle counter 165. During the time interval between two gate pulses following one another the CPU 161 reads out the data value of latch 164 and stores it in an internal random access memory (RAM). The scan counter 151 is controlled by programmable timer 163 for generating the linear addresses wherein one cycle typically has a duration of between 40 ms to 10 s. The number of events detected and registered between two gate pulses which may correspond to the beginning and to the end of one pixel in the spiral path or to a window in the scanned field is given by the difference of the content of counter 165 at $t_{in}$ and $t_{out}$ which are copied by latch 164 in response to each of the gate pulses (count($t_{out}$)−count($t_{in}$)).

Figure 2B:
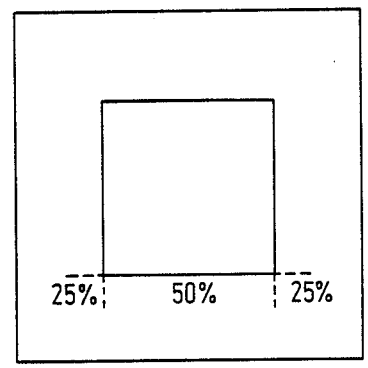
FIG. 2b illustrates a window of predetermined size of the linearly scanned field of FIG. 2a as known in the art.
Figure 3B:
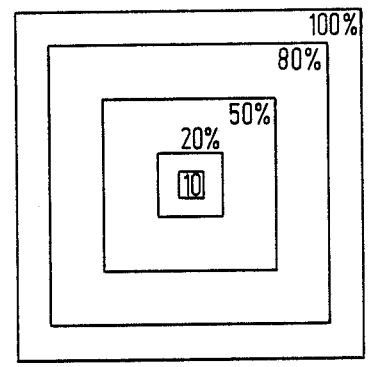
FIG. 3b shows a number of windows of predetermined size of the spirally scanned field of FIG. 3a in accordance with the present invention.

A number of windows with a differing percentage proportion of the entire test piece field are shown in FIG. 3b. Let it be supposed that as in the example of FIG. 2b, a 50% window is selected for the registration of the released secondary particles. If one assumes that the cycle time T embraces that period of time which the primary ionic beam needs to move from its starting point (left hand upper corner of FIG. 3a) into the center of the field and back again, this means that in a complete scanning cycle, which begins at a time $t_0$, the primary ionic beam is in the field outside the window up to a time $t_1 = 3T/8$. After the entry into the window at the time $t_1$ the primary ionic beam moves towards the center until it reaches it at time $t_2 = T/2$. At time $t_2$ the primary ionic beam turns round and returns in a spiral path, whereby it leaves the window at a time $t_3 = 5T/8$ and has returned to its starting point at a time $t_4 = T$.

This means that the primary ionic beam is within the window of the field for a time of $t_3 - t_1 = T/4$ without crossing the edge of the window. If one assumes, as in the example described above in conjunction with FIG. 2b, that it is necessary in order to prevent crater edge effects which cause errors to maintain a time period of one millisecond between the impact of the primary ion beam on the crater edge and the entry of the primary ion beam into the window, then a minimum cycle time of $T = 8/3$ milliseconds results, if the field is scanned twice or a time of $4/3 = 1.33$ milliseconds for a single scanning of the sample field. That means that the scanning velocity can be increased by a factor of 750 with the same position and sharp definition of the edge of the window.

A further advantage of the spiral scanning method is that it is possible without great difficulty as regards the registration device for the secondary particles separately to register the secondary ions released from the test piece field for windows of differing sizes arranged concentrically with one another because during the approach of the primary ionic beam from the starting point to the center and during its return only one entry time and one exit time need be taken into account for each of the windows, whereby the sharp definition for the edges of the windows is completely retained.

In the exemplary embodiment described above, the primary ionic beam describes a substantially square spiral path when scanning the test piece field and during scanning is guided firstly inwardly and then back again outwardly. The spiral scanning method may, however, be realized in a different manner, e.g. such that the primary ionic beam describes a substantially circular, eliptical or rectangular path. It is also possible to steer the primary ionic beam so that when scanning it is steered from its starting point in a spiral path to the center and then jumps back directly to its starting point without returning in a spiral path.

I claim:

1. A method of determining the composition of a solid body comprising creating a primary particle beam, directing said primary particle beam so as to impinge against said solid body and scanning said impinging beam in a raster over an area of said solid body so as to form a crater bounded by a boundary, whereby secondary particles are released from said solid body, and detecting and registering said secondary particles in dependence on the location of their release, and, in so doing, guiding said primary particle beam over said raster in a spiral path having convolutions and having an inner portion and an outer portion, said inner portion being remote from said boundary of said crater and said outer portion running generally parallel to and spaced from said boundary, and said outer portion of said spiral path having a length sufficient to cause a delay in time between the impingement at said boundary and the impingement at said inner portion sufficient to register the secondary particles released from said inner portion separately from the secondary particles released from said outer portion, whereby said determination may be based upon said registration of the secondary particles from said inner portion without distortion which would result if said registration of the secondary particles released from said inner portion were not made separately from that of the secondary particles released from said outer portion.

2. A method as claimed in claim 1, in which said step of guiding said primary particle beam is performed by guiding said primary particle beam over said raster inwardly along said spiral path and subsequently outwardly along a spiral path which may be the same as said spiral path or different therefrom.

3. A method as claimed in claim 1, in which said raster includes a plurality of concentric regions the boundaries between which are substantially parallel to adjacent portions of said spiral path, and in which said step of detecting and registering said secondary particles is performed by detecting and separately registering the released secondary particles by regions.

4. A method as claimed in claim 1, in which said step of creating a primary particle beam includes creating an ionic beam.

5. A method as claimed in claim 1, in which said step of detecting and registering said secondary particles includes detecting and registering ions.

6. A method as claimed in claim 1, including the step of using the results to obtain a depth profile of the distribution of one or more atomic or molecular concentrations in the body.

7. A method as claimed in claim 5, including the step of using the results to obtain a depth profile of the distribution of one or more atomic or molecular concentrations in the body.

8. A method as claimed in claim 1, including the step of using the results to obtain a mass or energy spectrum of the detected secondary particles.

9. A method as claimed in claim 5, including the step of using the results to obtain a mass or energy spectrum of the detected secondary particles.

10. A method as claimed in claim 1, in which said step of guiding said primary particle beam includes guiding said primary beam in a spiral path in which each convolution of the spiral path is of substantially rectangular shape.

11. A method as claimed in claim 1, in which said step of guiding said primary particle beam includes guiding said primary particle be in a spiral path in which each convolution of the spiral path is of substantially square shape.

12. A method as claimed in claim 1, in which said step of guiding said primary particle beam includes guiding said primary particle beam in a spiral path in which each convolution of the spiral path is of substantially circular shape.

* * * * *